United States Patent
Kopcienski et al.

(10) Patent No.: US 8,690,425 B2
(45) Date of Patent: *Apr. 8, 2014

(54) RETROFIT OF A MOBILE CART

(75) Inventors: John P. Kopcienski, Spencerport, NY (US); Robert J. Asento, Holley, NY (US)

(73) Assignee: Carestream Health, Inc., Rochester, NY (US)

( * ) Notice: Subject to any disclaimer, the term of this patent is extended or adjusted under 35 U.S.C. 154(b) by 542 days.

This patent is subject to a terminal disclaimer.

(21) Appl. No.: 12/948,829

(22) Filed: Nov. 18, 2010

(65) Prior Publication Data

US 2011/0123001 A1 May 26, 2011

Related U.S. Application Data

(60) Provisional application No. 61/264,288, filed on Nov. 25, 2009.

(51) Int. Cl.
*H05G 1/58* (2006.01)
*H05G 1/02* (2006.01)

(52) U.S. Cl.
USPC .......................... 378/198; 378/102; 378/116

(58) Field of Classification Search
USPC .................. 378/62, 102, 114–116, 197, 198
See application file for complete search history.

(56) References Cited

U.S. PATENT DOCUMENTS

| | | | |
|---|---|---|---|
| 7,016,467 B2 * | 3/2006 | Brooks | 378/102 |
| 7,224,769 B2 | 5/2007 | Turner | |
| D568,481 S | 5/2008 | Martinson | |
| 7,429,737 B2 * | 9/2008 | Wojcik et al. | 250/370.09 |
| 7,433,446 B2 | 10/2008 | Abe | |
| 7,434,997 B2 | 10/2008 | Koren | |
| 7,438,470 B2 | 10/2008 | Koren | |
| 7,573,034 B2 * | 8/2009 | Heath et al. | 250/361 R |
| 7,611,282 B2 * | 11/2009 | Koren et al. | 378/198 |
| 7,773,720 B2 * | 8/2010 | Honjo et al. | 378/19 |
| 7,844,031 B2 * | 11/2010 | Newman et al. | 378/114 |
| 7,909,511 B2 * | 3/2011 | Hall | 378/189 |
| 7,979,287 B2 * | 7/2011 | Amitani et al. | 705/2 |
| 8,085,901 B2 * | 12/2011 | Newman et al. | 378/114 |
| 2007/0140424 A1 | 6/2007 | Serceki | |
| 2007/0143147 A1 | 6/2007 | Petrick et al. | |
| 2008/0112535 A1 * | 5/2008 | Wojcik et al. | 378/62 |
| 2008/0240357 A1 | 10/2008 | Jabri et al. | |
| 2009/0034688 A1 | 2/2009 | Koren et al. | |
| 2009/0129546 A1 * | 5/2009 | Newman et al. | 378/114 |
| 2011/0096908 A1 * | 4/2011 | Newman et al. | 378/116 |
| 2011/0123001 A1 * | 5/2011 | Kopcienski et al. | 378/198 |
| 2012/0093295 A1 * | 4/2012 | Newman et al. | 378/114 |

* cited by examiner

*Primary Examiner* — Thomas R Artman

(57) ABSTRACT

Embodiments of methods and apparatus are disclosed for obtaining a digital dual mode mobile x-ray cart from an analog or single mode (e.g., film/CR) mobile x-ray cart. In some exemplary embodiments, a retrofit apparatus does not change interior components or certification of the single mode mobile x-ray imaging system. Further, a single operator switch can be used to initiate x-ray exposure in both operating modes.

20 Claims, 18 Drawing Sheets

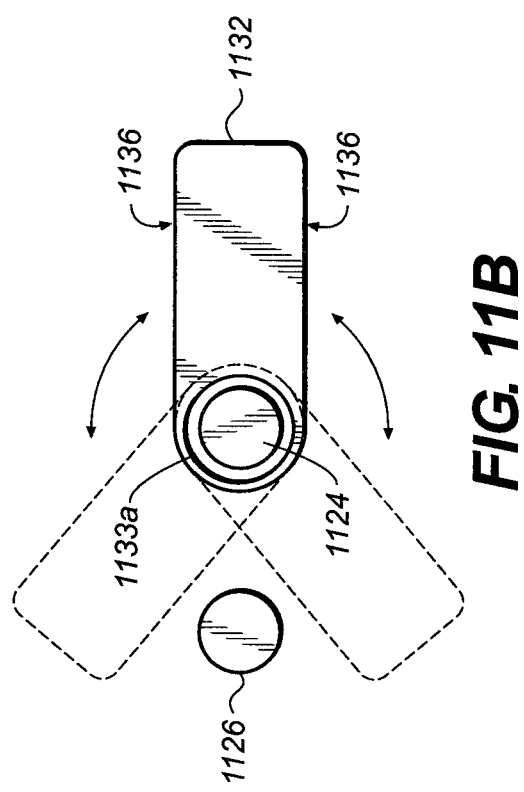

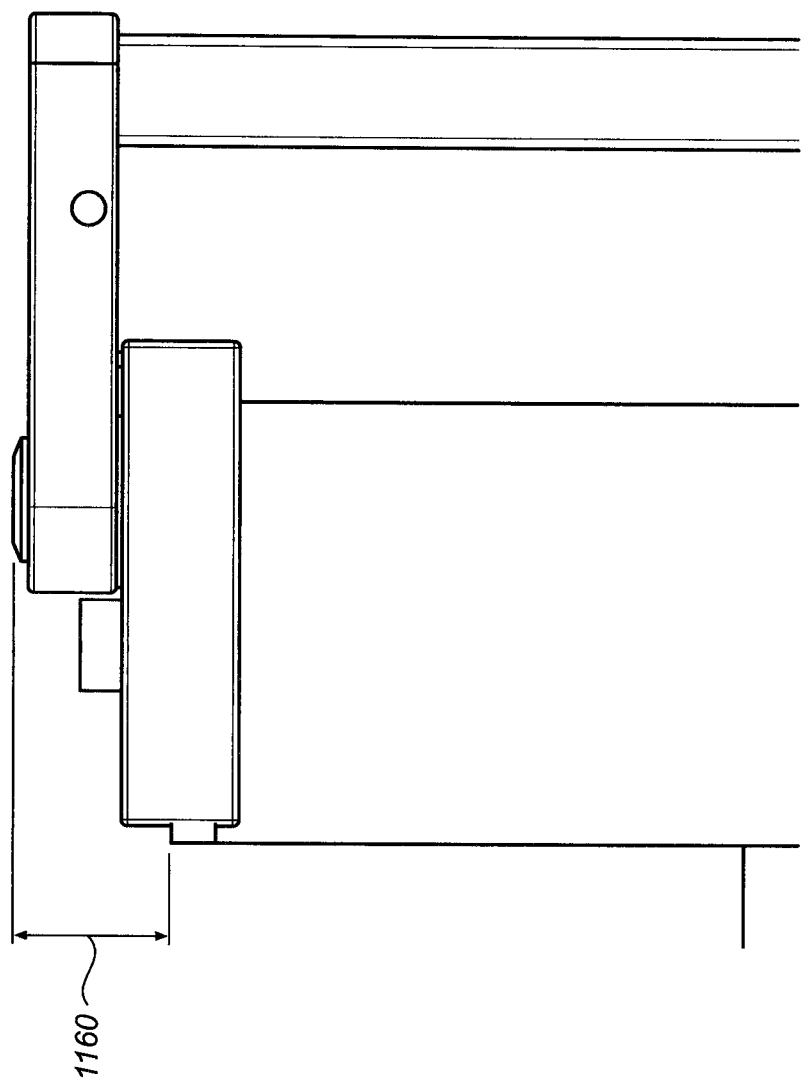

RETROFIT OF A MOBILE CART

CROSS REFERENCE TO RELATED APPLICATIONS

Priority is claimed from commonly assigned, copending U.S. provisional patent application Ser. No. (a) 61/264,288, filed Nov. 25, 2009, entitled "RETROFIT OF A MOBILE CART", in the name of Kopcienski, the disclosure of which is incorporated by reference.

FIELD OF THE INVENTION

The invention relates generally to the field of medical imaging, and in particular to a mobile cart for capturing analog and digital medical images.

BACKGROUND OF THE INVENTION

Mobile carts are employed in medical facilities to move medical equipment between locations. One type of mobile cart includes an x-ray source used to capture (analog) x-ray images on x-ray film. FIG. 1 shows a mobile cart with an x-ray source.

Refer also to commonly assigned U.S. Pat. No. 7,611,282 (Koren), U.S. Pat. No. 7,434,997 (Koren), and U.S. Pat. No. 7,438,470 (Koren).

SUMMARY OF THE INVENTION

Accordingly, it is an aspect of this application to address in whole or in part, at least the foregoing and other deficiencies in the related art.

It is another aspect of this application to provide in whole or in part, at least the advantages described herein.

Another aspect of the application is to provide a method by which an analog mobile cart can be modified to capture digital images.

Another aspect of the application is to provide a mobile x-ray system retrofit solution that is substantially non-invasive, reducing or eliminating the likelihood that inspection or re-certification of equipment by regulatory authorities would be required.

Another aspect of the application is to provide a mobile x-ray system retrofit solution that allows an x-ray system user to use one of selected imaging media types (e.g., film, CR) in addition to digital radiography (DR) receiver panels.

In one embodiment, a method for obtaining an image by using a digital radiography receiver in a mobile x-ray imaging system of a first type configured for film radiography or computed radiography (CR), can include providing a mobile x-ray imaging system of a first type configured for film radiography or CR, the mobile x-ray imaging system comprising a first portable power source for the first type mobile x-ray imaging system, providing a mobile retrofit connection apparatus to operate the mobile x-ray imaging system in a first mode for use with a digital radiography receiver by: forming a receiver interface for communicating signals to and from the digital radiography receiver, forming an operator interface for routing at least a first operator imaging signal from an operator control to the retrofit connection apparatus, transmitting at least a second imaging signal from the mobile retrofit connection apparatus to an x-ray generator of the x-ray imaging system, and providing a second portable power source for the retrofit connection apparatus, in response to the first operator imaging signal routed over the operator interface channel, transmitting the second imaging signal to the x-ray generator, and providing the mobile retrofit connection apparatus a second mode to operate the mobile x-ray imaging system for use with a film receiver or a CR cassette. In one embodiment, the mobile retrofit connection apparatus does not change interior components of the mobile x-ray imaging system used in the second mode.

In one embodiment, a apparatus configured to obtain an image using a second digital mode in a single mode mobile x-ray imaging system, can include an x-ray generator of a single mode mobile x-ray imaging system, a generator interface to communicate with the x-ray generator of the single mode mobile x-ray imaging system, a first portable power source for the single mode mobile x-ray imaging system, and an interface component installed as a retrofit to the single mode mobile x-ray imaging system, the interface component including a mode selector to select at least a first mode setting for image capture using a digital radiography receiver and a second mode setting for image capture using the single mode, a receiver interface to communicate with the digital radiography receiver, a second portable power source for the interface component, an operator interface to communicate with an operator control for receiving at least one imaging signal; and a programmed control logic processor that, when the first mode setting is selected, responds to the at least one imaging signal to control an exposure captured by the digital radiography receiver.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIGS. 2-3A shows components of exemplary kits for incorporation onto the analog mobile cart.

FIGS. 11A-11C shows portions of an exemplary mounting assembly for the DR display/controller in a retrofit apparatus according to embodiments of the application.

DESCRIPTION OF EXEMPLARY EMBODIMENTS

Figure 1:
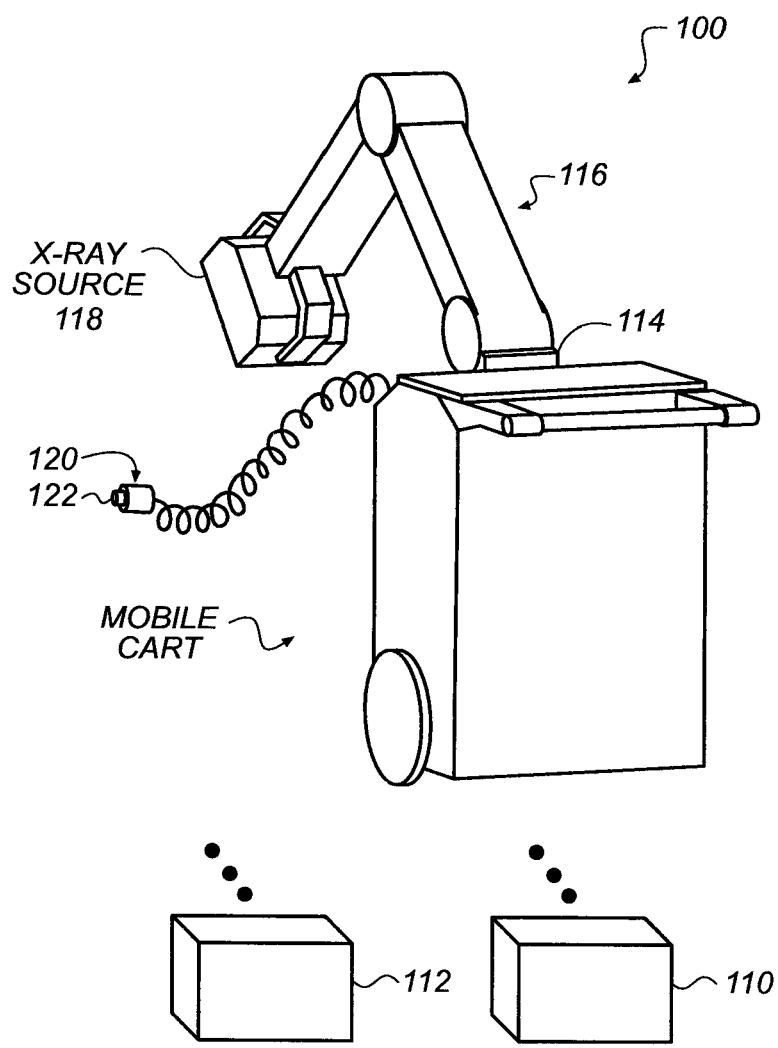
FIG. 1 shows a prior art analog mobile cart.

The following is a detailed description of the preferred embodiments of the invention, reference being made to the drawings in which the same reference numerals identify the same elements of structure in each of the several figures.

As noted above, mobile carts are employed in medical facilities to move medical equipment between locations. Referring again to FIG. 1 and FIG. 4, the analog mobile cart shown in this figure includes an x-ray source used to capture (analog) x-ray images on x-ray film.

Since digital radiography is being implemented in medical facilities, it may be desirable to have a mobile cart that includes digital radiography capability, that is, the ability to capture digital images.

Figure 2:
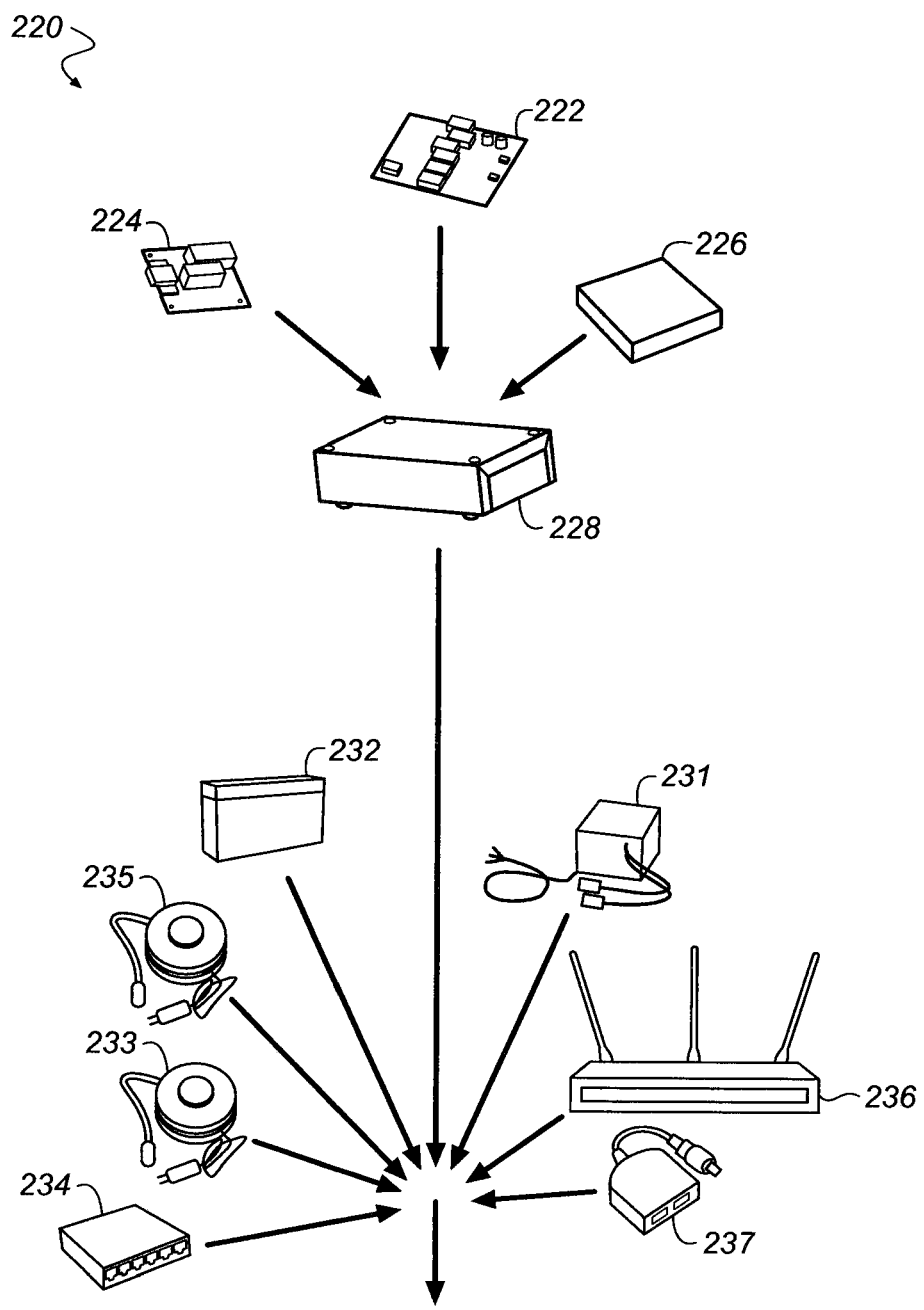

Referring to FIGS. 2 and 3, the present invention provides a method by which an analog mobile cart supporting the capture of analog images (i.e., an analog mobile cart) can be modified to support the capture of digital images (i.e., an analog/digital mobile cart). The method includes a "kit" of components which are added to the analog cart to create the analog/mobile cart.

As such, the kit provides a retrofit system for upgrading a mobile analog x-ray system to include a digital system.

The additional components are incorporated such that the electrical system of the analog cart is not compromised. Nor is the analog cart's power supply relied on to power the kit's additional components. With such incorporation, the safety and regulatory aspects of the cart are not affected. That is, there is provided a method to enable an analog mobile x-ray cart with digital radiography capability without relying on the analog cart's power or invalidating the cart's safety/regulatory approvals.

The kit provides the components, system control and mechanical packaging to connect to the cart without modifying the cart through the use of an independent power source (battery) and the re-use of existing cart fastener locations.

The analog mobile cart includes a power supply/battery to power the elements of the analog mobile cart.

The kit described herein includes another power supply/battery/charger which powers the components of the kit. Accordingly, the analog cart's power supply is not accessed/employed to power the kit's components. That is, there are two separate/distinct power supplies, each powering different components.

Figure 4:
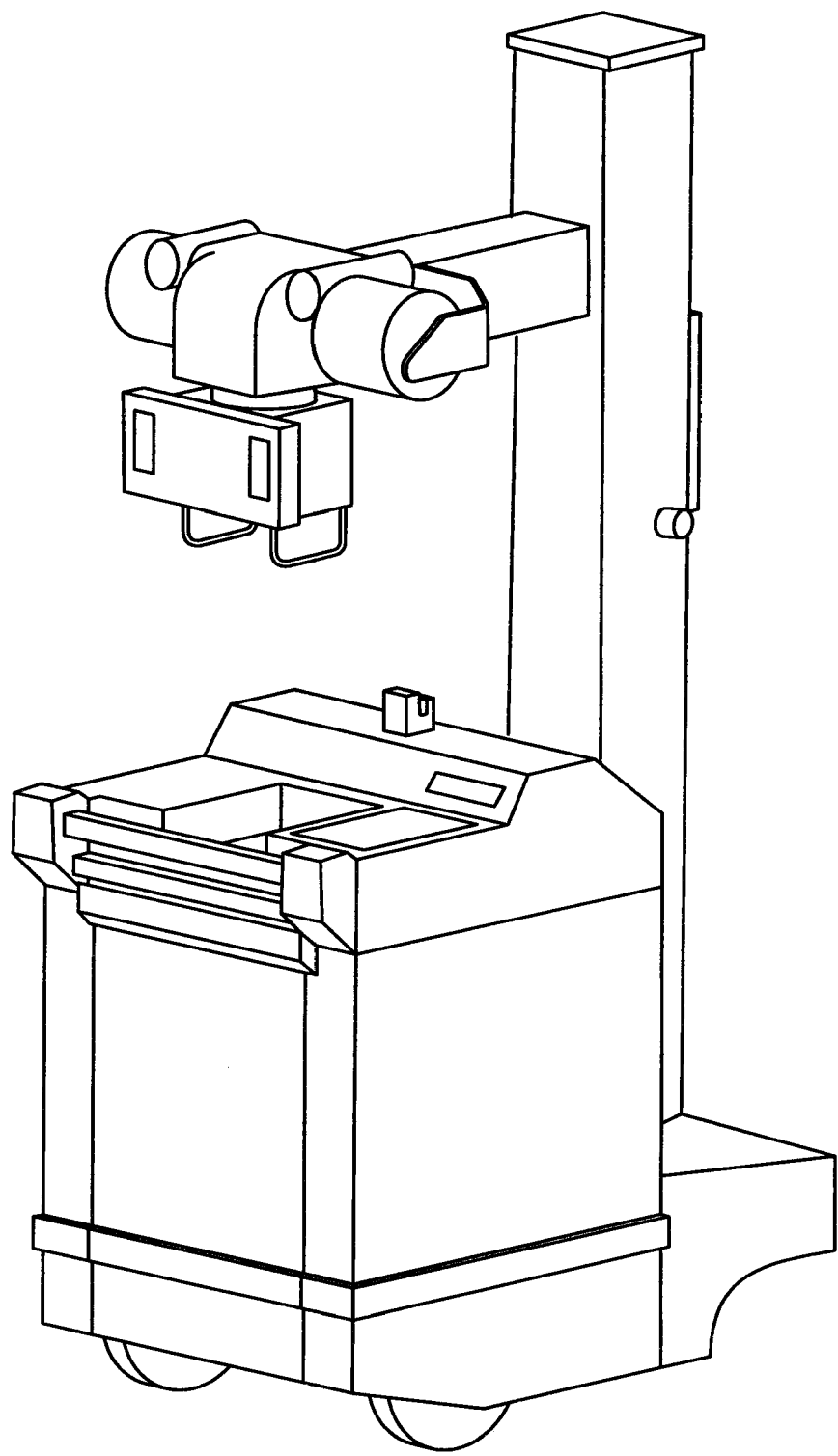
FIG. 4 shows another prior art analog mobile cart.
Figure 5:
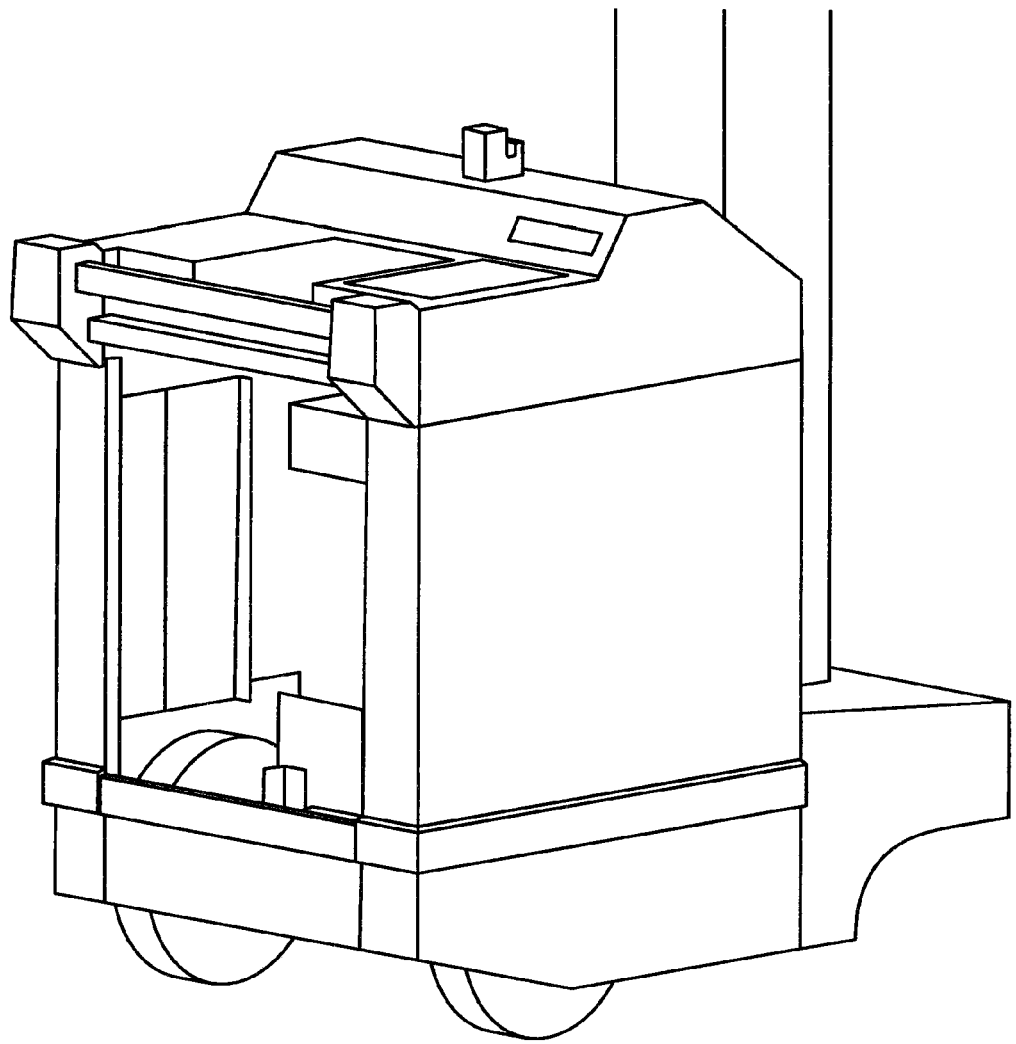
FIG. 5 shows portions of the interior of the analog cart, before incorporation of the kit's components.

The analog cart's power supply/battery (and charger) is typically located on the side of the unit. FIG. 4 illustrates a cover on the analog cart behind which is typically located the charger and batteries. The analog cart's AC power is supplied from a wall outlet through a cord attached to the cart and converted into DC power by the analog cart's charger to charge the analog cart's batteries. The analog cart's batteries provide power for the X-ray Generator, collimator light, and motors that power the analog cart's motion.

Figure 7:
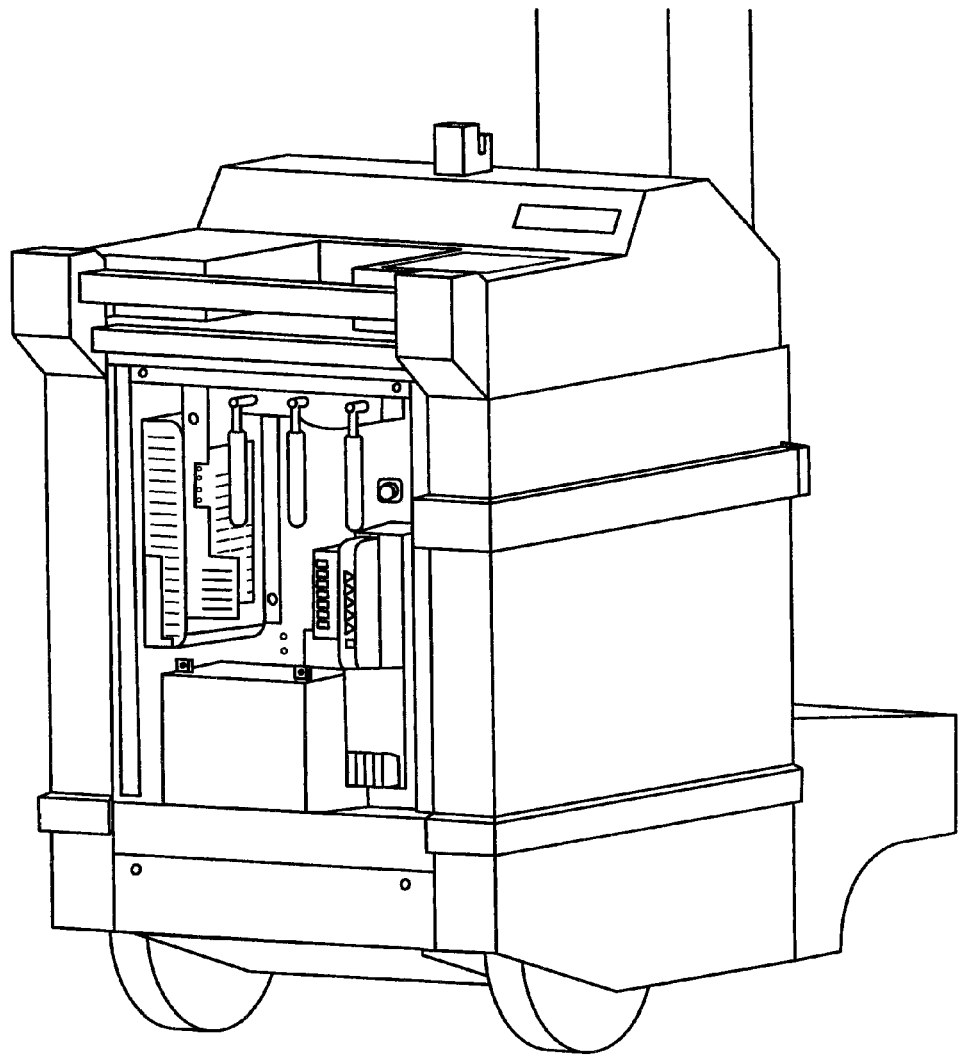
FIG. 7 shows portions of the analog/digital cart, after incorporation of the kit's components.
Figure 8:
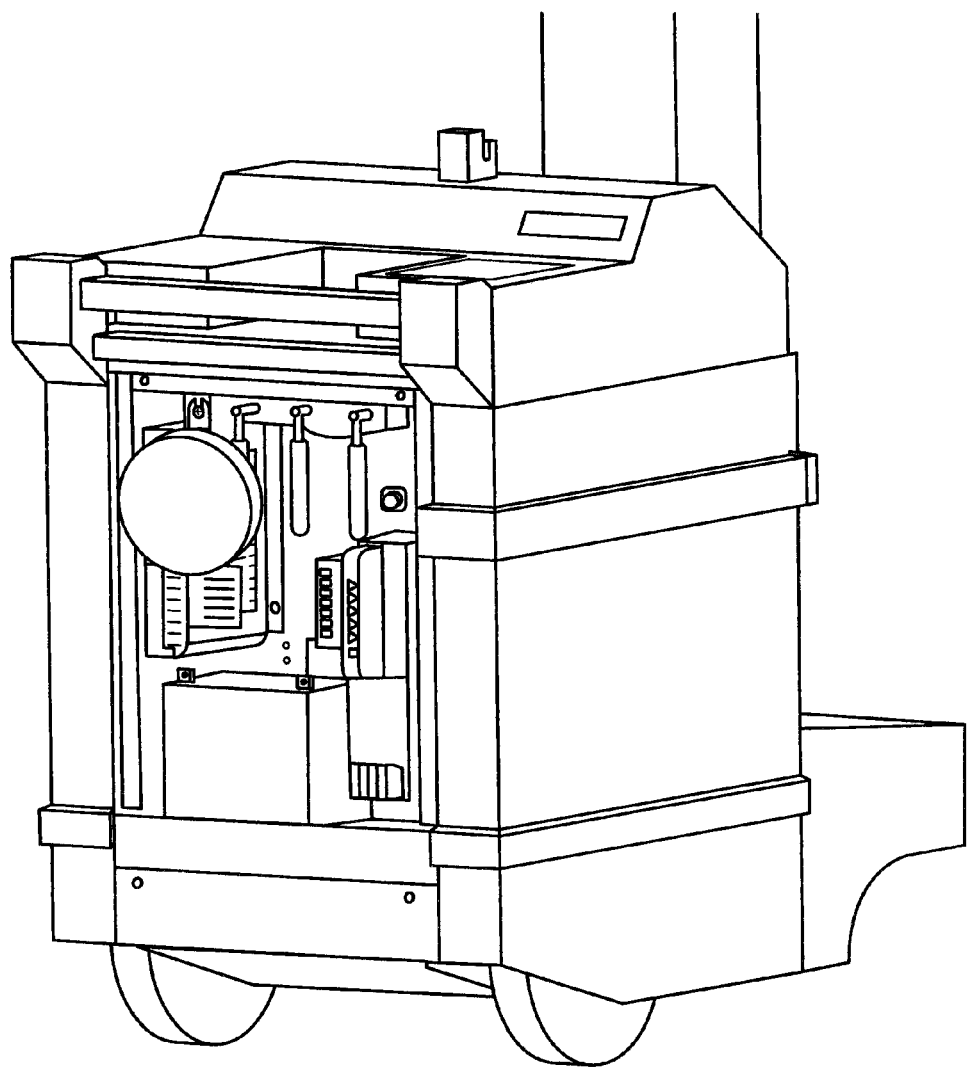
FIG. 8 shows portions of the analog/digital cart, after incorporation of the kit's components.

The power supply/charger and battery for the kit's components are separate. Referring to FIGS. 7 and 8, the power supply is positioned inside the cart. These figures show the location of the charger and batteries with the kit installed with the front bin removed. Note that the location can differ for different cart constructions.

The kit's AC power can be supplied from the wall outlet through a separate cord attached to the kit and converted into DC power by the kit charger to charge the kit battery. The kit's battery provides power for the kit's components (e.g., Computer, Wireless Access Point, Ethernet Switch, USB hub) to power all components necessary to power the digital imaging system.

The run time for the digital image capture may be dependent on the battery size chosen. For example, a kit battery that provides suitable power to run the kit for at about two hours.

Note that no power is drawn from the analog cart's batteries to run the kit's components. The incorporation of the kit's components does not connect to the analog cart's power system in any way. The only connection to the analog cart is the exposure switch that signals the generator to produce x-rays.

If the kit's battery enters a low voltage condition because of long term use, the kit's AC cord can be plugged into a wall outlet to provide continued run time.

The kit's components can include: Battery charger/UPS, Battery, AC cord reel (connects Battery Charger to AC power supply), Interface box (connects digital system to analog exposure switch input), DC to DC converter (for example, to convert 12 VDC to 5 VDC for other components), Ethernet Switch, USB hub, Wireless Access Point (communication between the PC and digital detector), Interconnect bulkhead (for Ethernet, USB and communications connections), Terminal strip for DC power distribution, and Fuses.

Once the kit is installed, it can include (on the front of the cart), a bin to cover the interior components and allow storage of the digital detector.

Once the kit is installed, it can include (on the top of the "tower" that supports the x-ray tube), a rotating bracket mounting/supporting the display and/or computer. A cover can enclose the display and motherboard into a self contained unit.

Cables connecting the computer and the components located in the bin area will preferably include a slack loop to allow for rotation of the mount and the x-ray source tower. The cables can pass through a wireway as they pass along side the mobile unit and continue into the bin area.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

FIG. 1 shows a conventional mobile film or analog x-ray system that can provide images on a media such as removable x-ray media. As shown in FIG. 1, mobile x-ray system 100 can use removable x-ray film 110 or removable CR cassette 112. Removable x-ray film 110 can also be provided in a cassette. Computed radiography (CR) cassettes 112 need to be removed after exposure to scan the x-ray image from imaging medium in a separate digital scanner. Films 110 need to be removed to be developed and checked, then physically transported to a selected location to be read. Removable film 110 or removable CR cassette 112 can have different standard sizes.

As shown in FIG. 1, an x-ray source 118 is adjustably mounted to the mobile x-ray system 100. In various configurations, the x-ray source 118 can be adjusted (e.g., positioned relative to a patient and/or x-ray detector) by an operator (e.g., x-ray technician) in three dimensions or in two dimensions. FIG. 1 illustrates a mounting arm 116 adjustable in two dimensions. FIG. 4 illustrates a mounting arm (e.g., tower) 416 adjustable in three dimensions. An operator control unit 114 can be used to set various parameters for an x-ray exposure using the x-ray source 118. Film 110 can be positioned adjacent and behind a patient to obtain an image during an exposure by the x-ray source 118.

An operator control switch 120 can be operatively connected to, and can operate as a part of, operator console 114. The operator control switch 120 can be variously embodied in different mobile x-ray systems. For example, the operator control switch 120 can be a two-position switch (e.g., push button) mounted on or near the operator console 114, two separate switches or other controls on or near the operator console 114, touch screen controls on or near the operator console 114, or a tethered hand switch connected by a cord or wire to allow the operator (e.g., x-ray technician) a larger range of movement. The operator control switch 120 can be wireless (e.g., IR, RF). The tethered hand switch can be coupled to the operator console 114 using a standard exemplary connector (e.g., USB connector, RJ11 connector, conductive line, etc.). As shown in FIG. 1, the operator control switch 120 is a tethered hand switch with a two-position push button switch 122.

The operator control switch 120 can transition the mobile X-ray system from an idle state to a preparation state, and from the preparation state to an exposure state. After being powered up, but before patient set-up and imaging, the mobile x-ray system 100 can be in the idle state. Once the patient is properly positioned for imaging, with cassette 110/112 in place, the operator can push switch 122 on the tethered hand switch 120 to advance to the preparation state, which can initiate the mobile x-ray system 100 to ready itself for an upcoming exposure. In some exemplary mobile x-ray systems, pressing a preparation switch, or otherwise entering a command to enter the preparation state, prepares the x-ray source for exposure (e.g., brings the rotor of an x-ray tube up to speed) as a preparatory action. The operator can set and hold the preparation state, for example, while waiting for the patient to get into the selected position for imaging. The operator can also "mash-through" the preparation and exposure switch 122 concurrently. Thus, the preparation state can last from less than a second (e.g., milliseconds) to a few seconds or even more than a minute.

In the preparation state or when the preparation state is complete, an exposure can be taken as soon as the operator advances switch 122 on the tethered hand switch 120 to an expose state or position to initiate an exposure (e.g., x-ray image, x-ray images or sequence of x-ray images and/or including dark frames) or exposure state. When the exposure is complete, the mobile x-ray system 100 can return to the idle state. Alternatively, the mobile x-ray system 100 can return to the preparation state after the exposure. For example, when the operator initiates the exposure using an expose switch, current goes to the anode of the x-ray tube, which can emit the ionizing radiation needed for exposure. At the conclusion of exposure, such as following a preset exposure time or when signaled by an Automatic Exposure Control (AEC) device or other exposure sensing device, both rotor and anode current are de-energized and the mobile x-ray system 100 transitions to the idle state. There can be a small system delay for the x-ray source 118 control circuitry, which can vary by the configuration (e.g., generator) of the existing mobile x-ray system when transitioning to the exposure state.

One aspect of embodiments of the application is to provide a retrofit apparatus and/or method for a first x-ray detection media type mobile x-ray system that enables alternative or exclusive use of a digital radiography receiver panel as the x-ray detector in place of the first x-ray detection media type (e.g., removable cassette 110/112).

In one embodiment, the retrofit apparatus can include a retrofit kit installed to an existing analog mobile x-ray system such as system 100.

Figure 3A:
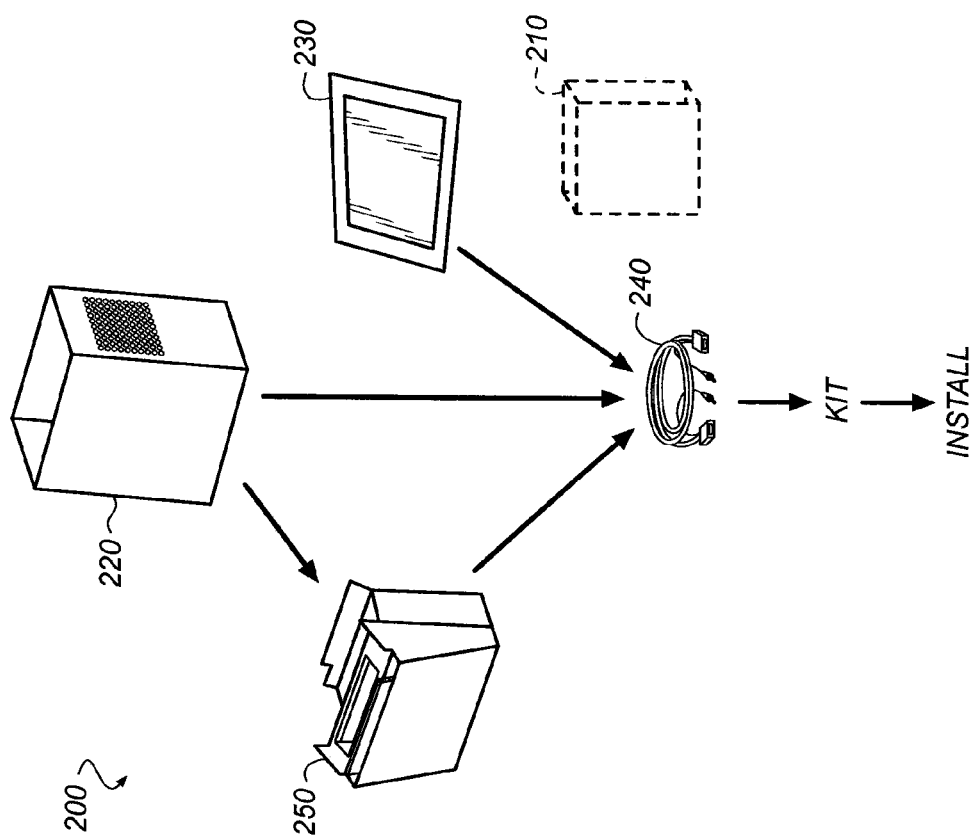

FIGS. 2-3A are diagrams that show an exemplary embodiment of a DR retrofit apparatus for a mobile x-ray system. As shown in FIG. 3A, a DR retrofit apparatus can comprise a retrofit kit 200 that can include an optional DR detector 210, a DR operator console (e.g., display/processor) 230, a power and communications unit 220, connecting cables 240 and a replacement front panel 250. The cables 240 can provide a physical communication path between the power and communications unit 220 and the DR operator console 230. In addition, the cables 240 can optionally provide/support communications to and/or from the DR detector 210.

Figure 3B:
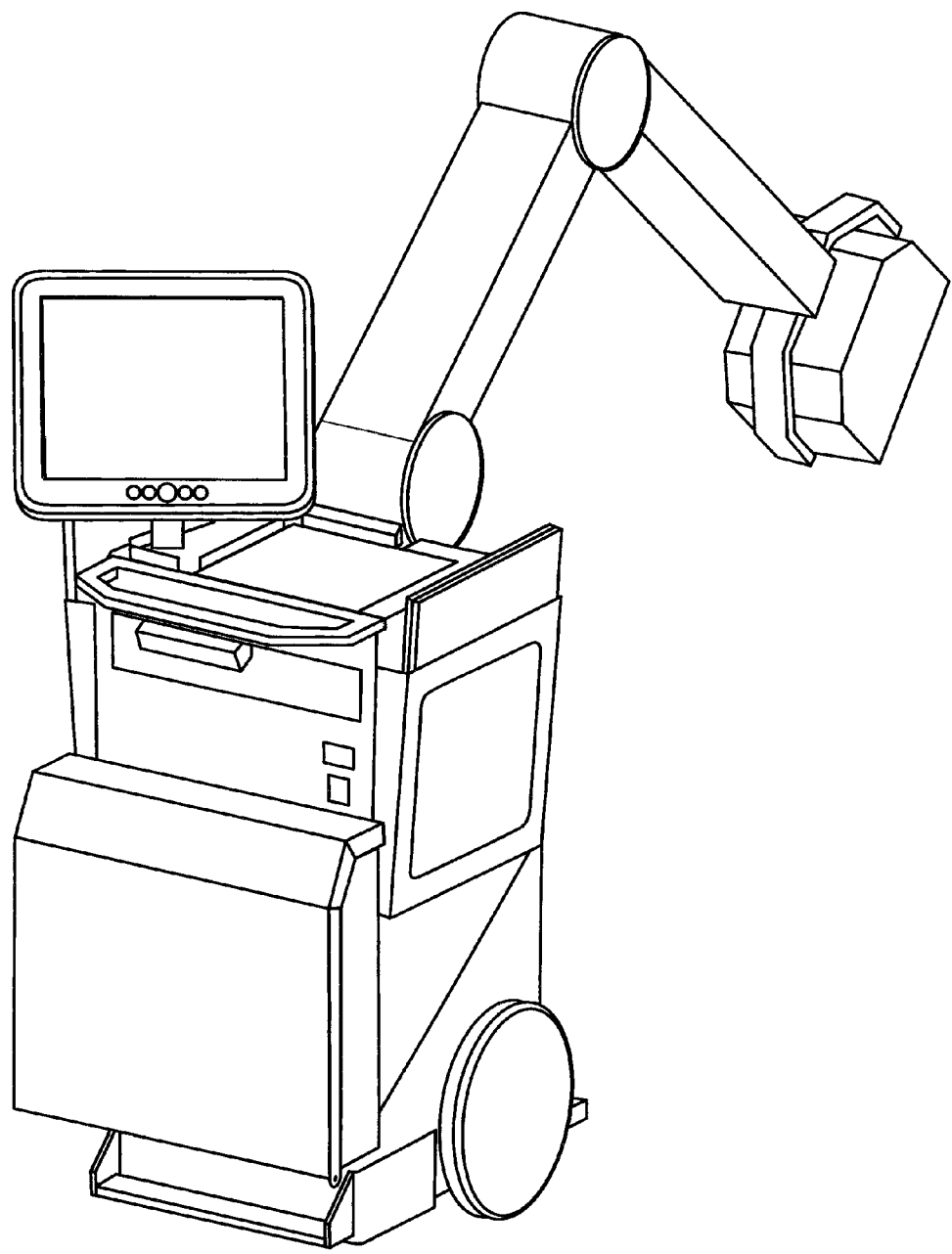
FIGS. 3B-3C are diagrams that show exemplary first type mobile x-ray systems including an embodiment of a retrofit apparatus in accordance with the application.
Figure 3C:
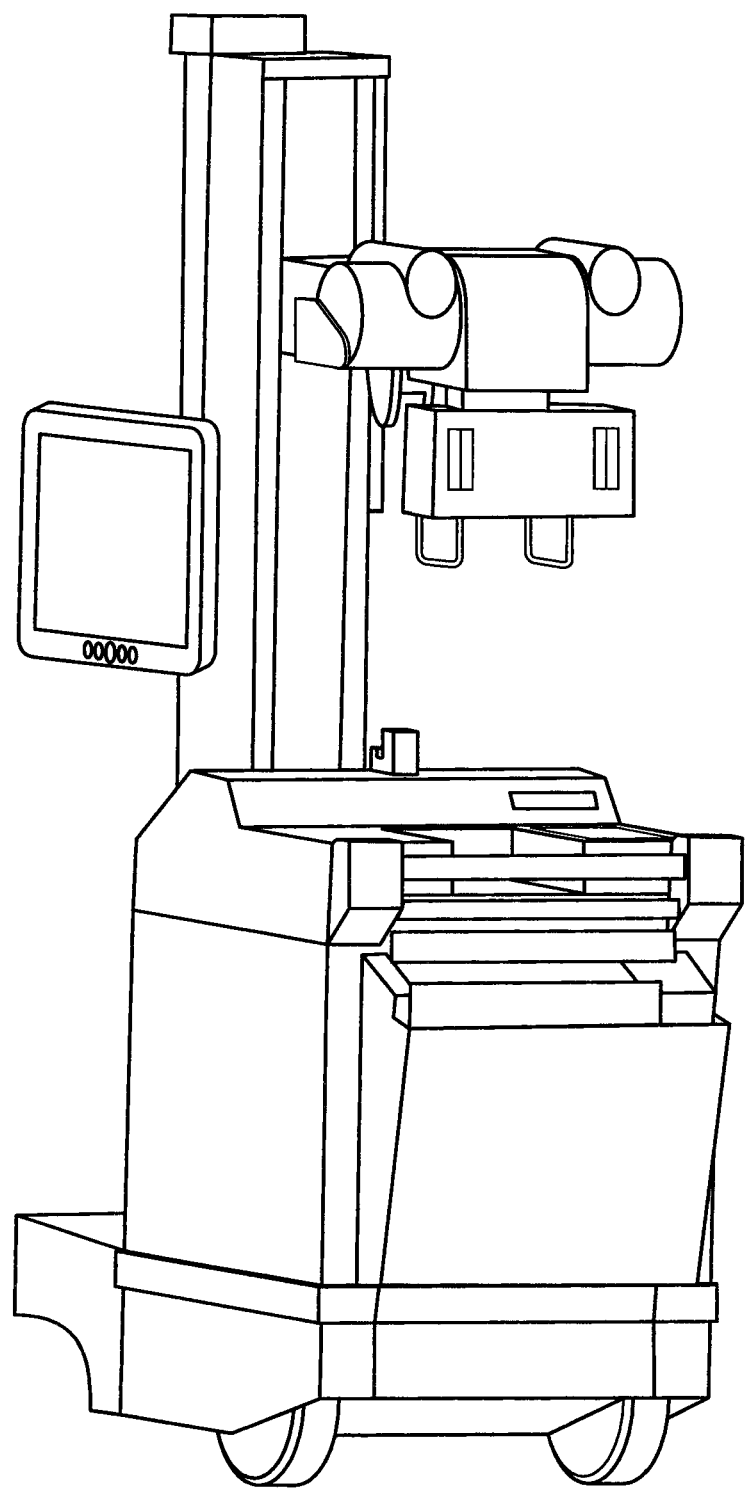

FIGS. 3B-3C are diagrams that show exemplary first type mobile x-ray systems (e.g., OEM mobile x-ray systems) having an embodiment of a retrofit apparatus in accordance with the application installed. The first type mobile x-ray system shown in FIG. 3C can be motorized.

FIG. 2 is a diagram that shows an exemplary power and communications unit for a retrofit apparatus in accordance with embodiments of the application. As shown in FIG. 2, a power and communications unit 220 can include interface board 222, tether board 224, optional voltage converters 226, a battery charger 231, a battery 232, power reel 233, Ethernet switch 234, optional Ethernet reel 235, wireless Access Point (AP) 236, and USB hub 237.

The power and communication unit 220 can convert an operator signal from the operator control switch 120, based on the mode selected, to a signal to send to the DR operator console 230 in a digital mode or pass the operator signal (e.g., unchanged) when a first mode (e.g., film/CR mode) is selected. The power and communication unit 220 can further provide power to the components of the retrofit kit 200 or only to components of the retrofit kit 200. The power and communication unit 220 can provide communications between the DR operator console 230 and external systems/processors or X-ray detectors (e.g., DR detectors 210).

A mode selection switch can be implemented in the retrofit apparatus 200. The mode selection switch can change the retrofitted mobile x-ray system operating mode between the original mode (e.g., first or film/CR mode) and the DR mode (e.g., second mode) added by the installed retrofit kit 200. In one embodiment, the mode selection switch can be exposed on the front panel 250.

The interface board 222, the tether board 224 and one or more optional voltages converters 226 (e.g., 12V to 5V converter) can be separately installed or assembled as a single unit 228. Interface board 222 can be coupled to the tether board 224, which can be used to provide an interface for wired or direct connection to the DR detector 210. The physical connection supplied through the tether board 224 can be for image recovery from the DR detector 210. The interface board 222 can further connect to provide a plurality of local networks or connections. Thus, the interface board 224 (or unit 228) can connect to the USB hub 237, the AP 236 and/or the Ethernet switch 234. In one embodiment, the AP 236 provides a wireless interface to the DR detector 210 and can be wired to the DR operator console 230. Thus, the x-ray data from the DR detector 210 can be wirelessly transmitted to the DR console 230 for display, review, adjustment and/or storage. The Ethernet switch 234 can be separately wired from the power and communication unit 220 to the DR operator console 230.

The retrofit kit 200 further can allow external communications from the DR console 230, such as but not limited to transmitting images from the DR detector 210 to a remote site (e.g., an external processor, hospital, etc.). Alternatively, the interface to the hospital can be implemented using a wired connection such as an Ethernet cable or the like. In one embodiment, the installed retrofit kit 200 can include Ethernet reel 234 to implement direct connection to an exterior processor such as a processor in the radiology department in a hospital. Alternatively, the exterior system can provide a standard wired cable such as a USB or Ethernet cable for connection to a standard connector provided by the retrofit apparatus 200 (e.g., exposed in the replacement front panel 250).

The Ethernet switch 234 can used to couple a connector to the DR detector wired access point or wired connection or tether to the DR detector 210. In operation, the DR detector 210 can have its wireless interface and its wired interface active. If wireless communications are lost, the wired connection can be used to retrieve images from the DR detector 210 to the DR console 230/hospital.

Cables 246 are used to transmit/receive data, communications, or control information to/from the DR console 230. Preferably, few cables 246 (e.g., power, data, control) are used to connect the power and communication unit 220 to the DR operator console 230 and provide wired communication therebetween. In one embodiment, at least one wired line connects from a processor (e.g., NIC cards) in the DR console 230 to accommodate the DR detector 210 through the AP 236 (e.g., via the USB hub 237) and at least one wired line connects the DR console 230 to the Ethernet switch 235 in the power and communication unit 220. The USB hub 237/the Ethernet switch 235 can be used for connection of a ID code reader (not shown). In addition, at least one power cable can connect the DR console 230 to the power and communication unit 220.

The battery charger 231 can be used to charge the battery 232. The battery charger can be connected to the power reel 233, which can be connected to exterior power sources to charge the battery 232. The battery 232 (e.g., 12 volt, lead acid rechargeable battery, rechargeable lithium battery, etc.) can be used to provide power to operate components of the retrofit apparatus 200 after installation to a retrofitted dual mode mobile x-ray system (e.g., see FIG. 3B, 3C or 6). Thus, the battery 232 can be used to power retrofit apparatus 200 components such as the installed replacement panel 250, other components of the power and communication unit 220, the digital operator console 230, or charge the DR detector 210 mounted in the replacement panel 250 (e.g., mounted to the installed retrofit kit 200).

The front panel 250 can be used to replace a front panel or side panel on the existing initial first type mobile x-ray cart and can include at least locations to store cassettes 110, 112 and DR detectors 210 of various sizes, a battery charge indicator (e.g., visible light gauge), exposed external power connect or power reel 233, ID code reader connector and a connector for the operator control switch 120 (e.g., connector for the existing tethered operator control switch 120. The retrofit apparatus 200 can be installed by connecting the operator control switch 120 into an interface/connector between the original equipment switch (e.g., preparation/exposure switch 122) and its original equipment connection. Accordingly, in one embodiment the retrofit kit 200 can be installed by unplugging the original equipment preparation/exposure switch 122, plug the power and communication unit 220 into the uncovered connector (e.g., 922) that received the original equipment preparation/exposure switch 122 (e.g., on tethered operator control switch 120), and plug the operator control switch 120 into the power and communication unit 220. After the retrofit kit 200 is installed, in both the first analog mode or the second digital mode, the operator can manually use the original equipment preparation/exposure switch 122. In one embodiment, the front panel 250 can include one or more different sized recharging mounts for the DR detectors 210.

Figure 9:
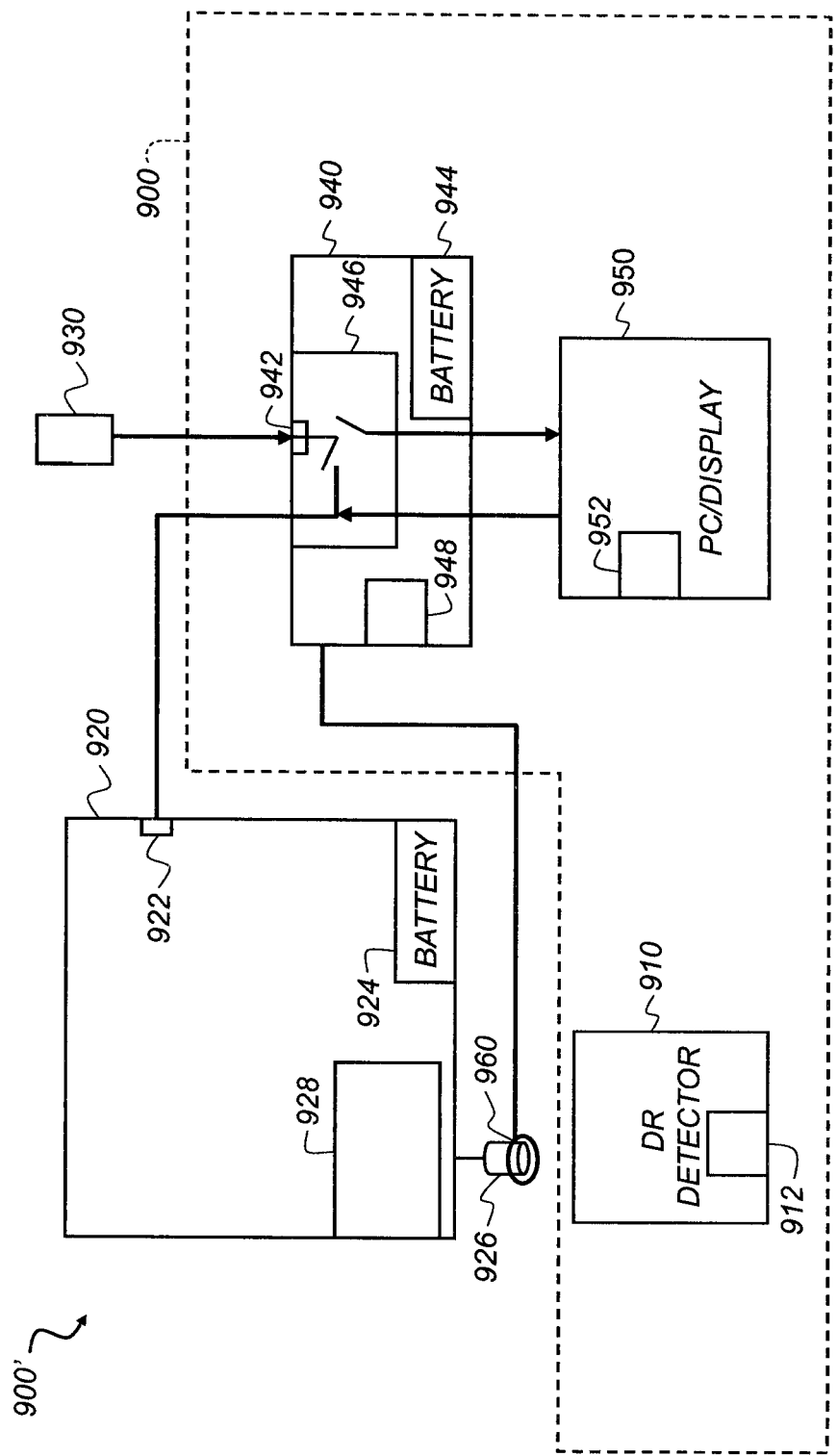
FIG. 9 is a diagram that shows an exemplary digital retrofit mobile x-ray imaging apparatus in accordance with embodiments of the application.

FIG. 9 is a diagram that shows an exemplary digital retrofit mobile x-ray imaging apparatus in accordance with embodiments of the application. As shown in FIG. 9, an exemplary embodiment of a digital retrofit mobile x-ray imaging apparatus 900 can selectively substitute a digital radiography detector (e.g., wireless or wired) 910 in place of film/CR cassettes and implement corresponding changes to an exterior of a first type mobile x-ray cart 920, without modifying internal components thereof, by replacing only external parts thereof, by using existing fasteners, or by coupling to an operator switch connector 922 of the mobile x-ray cart 920. For example, the connector 922 can be exposed in an exterior of the first type mobile x-ray cart 920. A digital interface controller 940 can communicate between the DR detector 910 and the DR console 950. Image data from the DR detector 910 can go to an imaging processor 952 that can be part of (or in communication with) a PC/display processor in the DR console 950. The digital interface controller 940 can connect between an operator switch (e.g., original equipment switch) 930 and the operator switch connector 922.

An interface control unit 946 can be used to route preparation signals and exposure signals from an operator switch 930 directly to the mobile x-ray cart 920 or via DR console 950 to the first type mobile x-ray cart 920 in accordance with the selected mode of operation of the digital retrofit mobile x-ray imaging system 900. In one embodiment, the digital retrofit mobile x-ray imaging apparatus 900 can operate in a first mode for x-ray film/CR media and pass the switch 930 signals unchanged and can operate in a second mode where the DR detector 210 is used by the first type mobile x-ray cart 920 and the switch 930 signals are interrupted (e.g., delayed for communications with DR detector 910) by the digital retrofit mobile x-ray imaging apparatus 900. In one embodiment, pressing the exposure switch in the second mode can cause the DR console 950 to send a reset signal to the DR detector 910. Reset of the DR detector image-sensing circuitry can take little time (e.g., about 300 milliseconds). An optional reset acknowledgement signal is received from the DR detector 910 when reset has been completed. In one embodiment, the reset acknowledgement is required before x-rays are generated and anode current is provided to help to prevent exposing the patient to the x-ray radiation when the DR detector 910 is not ready to form an image. An additional delay period can be caused by x-ray generator control circuitry and represents the timing interval between the time integration begins at the DR receiver panel and the time x-rays are emitted (anode current ON). This additional delay period can depend on the specific x-ray generator used and/or whether the preparation state was completed (e.g., contrast with button mash through). In one embodiment, the DR console 950 can address both delay periods described herein upon receipt of the exposure signal before forwarding the exposure signal to the mobile x-ray cart 920. The operator control switch 930 can be connected to the digital interface controller 940 by connector 942 (e.g., tether, infrared, wireless). In one embodiment, the connector 932 is the same connector type as the connector 922 on mobile x-ray cart 920 and the original operator switch of the mobile x-ray cart 920 is re-used for the operator switch 930.

A DR detector interface or communications channel can be between the DR detector 910 and an interface 948 on digital interface controller 940. A transceiver 912 can be connected to or provided and part of the DR detector 910 to communicate with a transceiver that is part of or connected to the interface 948. In one embodiment, a first power source 924 (e.g., battery, charger, AC connector, DC voltage converter) can be provided with the mobile x-ray cart 920, which can be motorized, to provide power for operations of the mobile x-ray cart 920. A second separate independent power source 944 (e.g., battery, charger, AC connector, DC voltage converter) can be provided with the digital mode system (e.g., 940, 950, 910) to provide power for operations of the digital retrofit mobile x-ray imaging apparatus 900.

X-ray generator control signals can pass from the mobile x-ray cart 920 to the x-ray source 926. An optional sensor 960 can be provide for operable connection to the x-ray source 926 to detect active x-ray emission from the x-ray source 926. For example anode current sensing by sensor 960 can be used to control/initiate/terminate signal integration for the DR detector 910. Such an additional non-invasive sensor 960 can be implemented rather than an invasive detection of signals to/from the x-ray source 926 from a controller 928 of the mobile x-ray cart 920. As is well known in the art of x-ray imaging, a number of additional conditions can be satisfied prior to activate the x-ray source 926 (e.g., allow the flow of anode current to the x-ray tube). These conditions can include, for example, requirements that equipment interlock conditions be satisfied.

The DR console 950 can be physically mounted to the mobile x-ray cart 920. In one embodiment, the DR console 950 is mounted to rotate to at least 90°, 180°, 270° or more independent of the mobile x-ray cart 920. The DR console 950 can be mounted to a surface of a main body of the mobile x-ray cart 920 to rotate with and independent of rotation of the mobile x-ray cart 920. Alternatively, the DR console 950 can be mounted to a tower of the mobile x-ray cart 920 to rotate with rotation of the tower and to rotate independent of the tower (e.g., independent rotation of at least 90°, 180°, and 270°).

As shown in FIG. 9, a retrofitted dual mode mobile x-ray imaging system 900' can operate in a first mode for x-ray film/CR media and can operate in a second mode where the DR detector 910 is used with the DR console 950 and the first type mobile x-ray cart 920. The retrofitted dual mode mobile x-ray imaging system 900' can use a first power source for the first type mobile x-ray cart 920 and a second power source for the digital retrofit mobile x-ray imaging apparatus 900.

Figure 10:
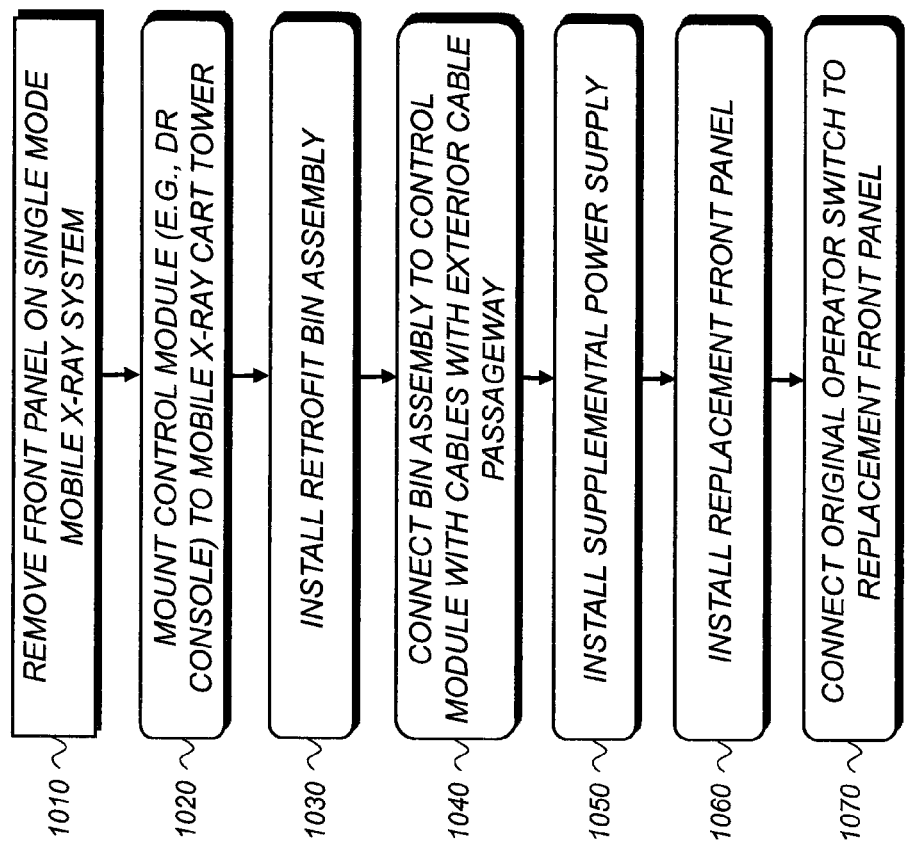
FIG. 10 is a flow chart that shows an exemplary method of retrofitting a single mode mobile x-ray cart according to embodiments of the application.

Referring to FIG. 10, a flow chart that shows an exemplary method of modifying a single mode mobile x-ray cart to a digital, independently powered, dual mode mobile x-ray cart according to embodiments of the application will now be described. The method for modifying a single mode mobile x-ray cart will be described using embodiments of retrofit apparatus/kits shown in FIGS. 2-3A and 9 and can be applied to mobile x-ray systems/carts shown in FIGS. 1 and 4-8; however, the method of FIG. 10 is not intended to be limited thereby.

As shown in FIG. 10, a panel such as a front panel 410 (e.g., see FIG. 4) or the panel including the existing bin of the mobile x-ray system 100 can be removed to gain access to the interior of the mobile x-ray cart. Preferably, the removed fasteners (e.g., screws, nuts and bolts, etc.) can be reused (operation block 1010).

Figure 6:
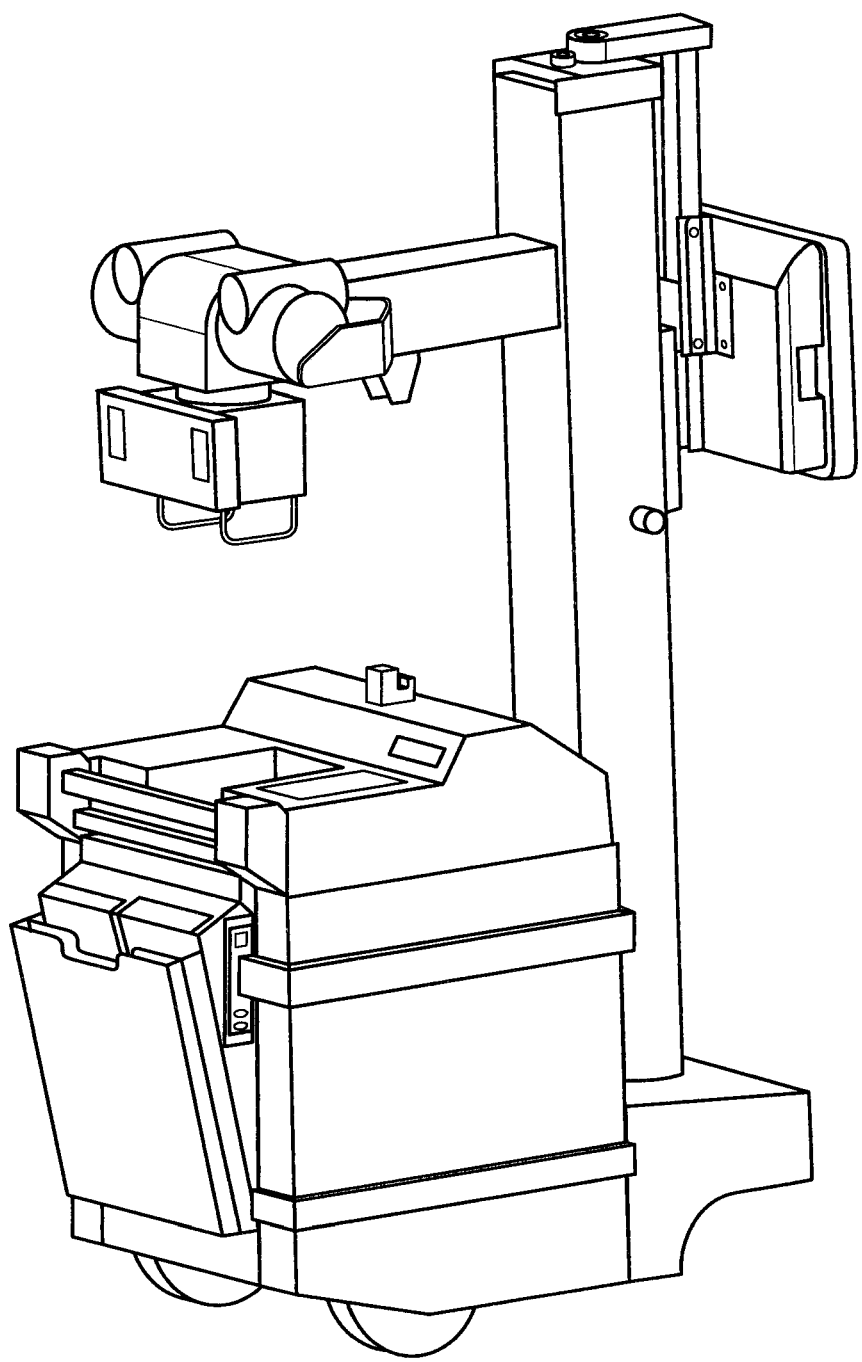
FIG. 6 shows portions of the analog/digital cart, after incorporation of the kit's components.

Then, the DR console or DR control module (e.g., 230, 950) can be installed to the mobile x-ray system. As shown in FIG. 6, a top/cover plate 420 (e.g., see FIG. 4) of the tower can be removed and replaced with a retrofit mounting plate 610 (e.g., to affix the DR console or all in one PC/display). Again preferably, the removed fasteners can be reused. A mounting arm including the DR console is then rotatably attached to the retrofit mounting plate 610 on the mobile x-ray system tower (operation block 1020). As shown in FIG. 3C, the mounting plate and mounting arm can provide greater than 180 degrees movement of the DR console around the tower in addition to allowing the DR console to move (rotate) with rotation of the tower.

A bin assembly (e.g., power and communication unit 220) can be installed in an open interior (e.g., see FIG. 5) accessed by the removal of the front panel of the single mode mobile x-ray cart. The previously removed fasteners can be used (operation block 1030). Alternatively, individual components of the retrofit kit 200 (e.g., power and communication unit 220) can be installed in the open interior of the single mode mobile x-ray cart shown in FIG. 5.

Then, the bin assembly can be connected (e.g., cables 240) to the DR console. Although wireless connection can be used, in exemplary embodiments, the DR console can be electrically connected to components in the bin assembly using wires/cables (operation block 1040). For example, cables (e.g., USB, Ethernet, power, etc.) can be installed via an exterior mounted passageway 620 around the body of the single mode mobile x-ray cart and covered by a sleeve to cross a distance from the mobile x-ray cart body to the DR console. Preferably, the exterior mounted passageway 620 can be attached to side and/or back panels using existing fastener holes.

A supplementary power source (e.g., battery, AC plug, charger, voltage converter) to power components of the bin assembly and DR console is installed as part of the retrofit apparatus (operation block 1050). The digital power source can be installed to the interior of the single mode mobile x-ray cart or installed to the bin assembly.

A replacement front cover can then be installed to the bin assembly or the exposed fastener recess of the single mode mobile x-ray cart. Preferable, a supplemental power supply connector (e.g., extendable plug) can be mounted to be exposed and secured to the replacement front panel (operation block 1060).

Then, the original equipment hand switch and hand switch cable can be installed or connected to an exposed connector (e.g., standard connector) in the replacement front panel (operation block 1070). Alternatively, a new operator switch can be installed, but the same operator switch can be used for both original mode and the digital mode of the converted digital, independently powered, dual mode mobile x-ray cart.

Figure 11A:
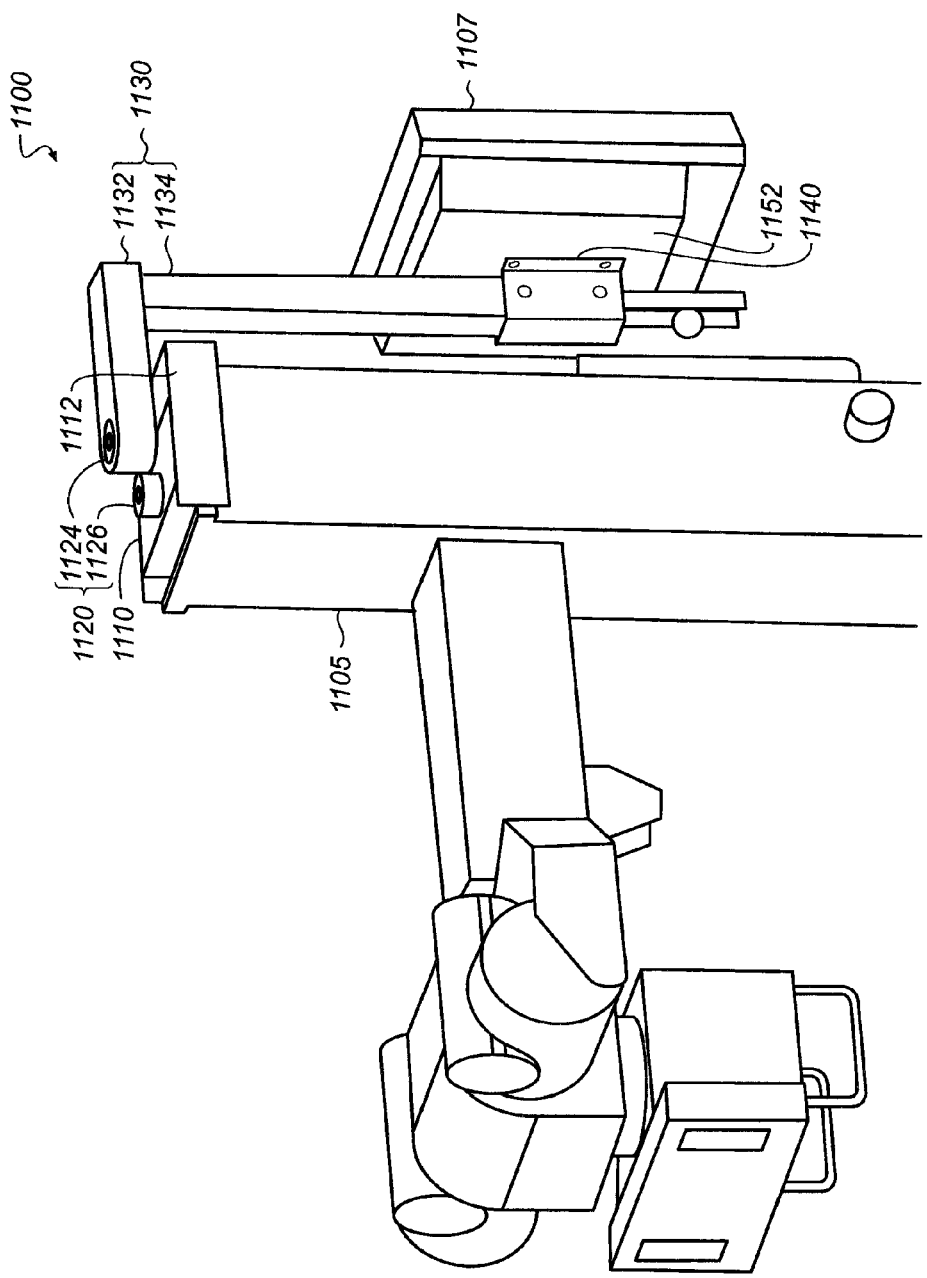

FIGS. 11A-11C are diagrams that illustrate an exemplary embodiment of a mounting assembly of a DR console for a retrofit DR dual mode mobile x-ray cart. As shown in FIG. 11A, a mounting assembly 1100 can connect a DR console (e.g., a PC and touch screen monitor in one package) to rotate independently from a tube tower of the retrofit mobile x-ray cart and also rotate concurrently along with rotation of the tube tower to allow operator (e.g. x-ray technician) desired positioning of the DR console. As shown in FIG. 11A, an x-ray generator can be adjusted in three dimensions using the tube tower rotation and two additional telescoping arms. The mounting assembly 1100 can install without modifying an exterior of the tower, interior components and/or certification of the retrofit mobile x-ray cart (e.g., using existing engagement holes in a tube tower).

As shown in FIG. 11A, the mounting assembly can include a first connecting unit 1110, an engagement unit 1120 (e.g., extending pin (for rotation) and rotation stopper), a mounting arm 1130 rotatably attached to the engagement unit 1120, and a mounting bracket 1140, which can affix the DR console 1107 to the mounting arm 1130. In one exemplary embodiment, the first connecting unit 1110 can include a cover plate 1112 to connect to existing engagement recesses in a tube tower 1105. The cover plate 1112 can includes holes for threaded or nut/bolt connection to the existing recesses (e.g., original cover plate screw holes) in the tube tower 1105. For example, such existing engagement holes can be located on a top surface of the tube tower or on side surfaces of the tube tower near the top surface. The engagement unit 1120 can be rigidly attached to or integral with the cover plate 1112.

The engagement unit 1120 can include a first projection or extending pin 1124 to allow independent rotational connection of the mounting arm 1130 and a second projection or stopper 1126 to limit the independent rotational movement of the mounting arm 1130. As shown in FIG. 11B, the mounting arm 1130 can freely rotate around first pin 1124 until a side surface 1136 of the mounting arm 1130 contacts the second pin 1126.

The mounting arm 1130 can include a first arm 1132 with a first end in rotating attachment to the engagement unit 1120 and a second arm 1134 to connect to the mounting bracket 1140. For example, the first end of the mounting first arm 1132 can include a circular though-hole 1133a that can surround and slidingly pivot around the first projection pin 1124. The second end of the first arm 1132 can extend horizontally beyond the dimensions of the tube tower 1105 to a connection point for the second arm 1134. The second arm 1134 can extend vertically to the bracket 1140, which can be rigidly attached on a back side 1152 of the DR console 1107. Threaded screws, nuts and bolts can connect respective portions of the mounting assembly 1100; however, other fasteners such as mechanical fasteners, rivets, bonds, welds, nails, hook and loop connectors, adhesives, epoxys as conventionally known can be used.

Figure 12:
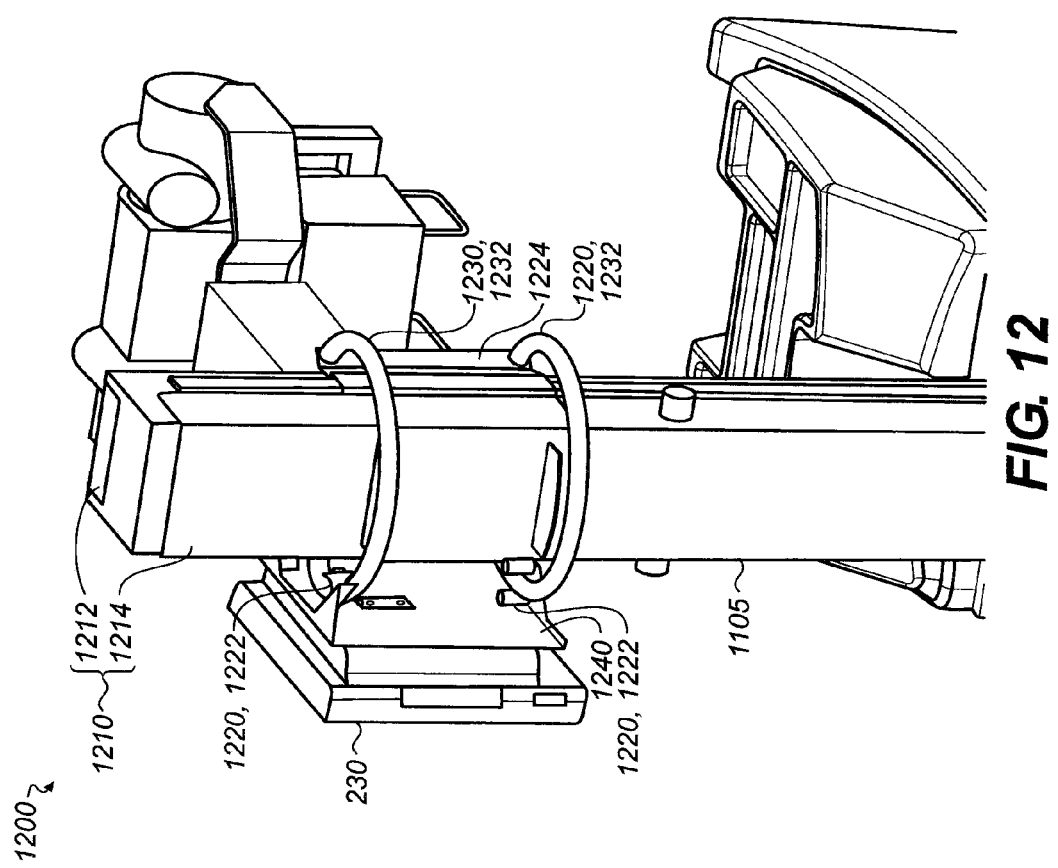
FIG. 12 is a diagram that shows another exemplary mounting assembly for the DR display/controller in a retrofit apparatus according to embodiments of the application.

FIG. 12 is a diagram that illustrates another exemplary embodiment of a mounting assembly of a DR console for a retrofit DR dual mode mobile x-ray cart. As shown in FIG. 12, a mounting assembly 1200 can connect to a DR console to rotate independently from a retrofit mobile x-ray cart and concurrently with the tube tower 1105 of the retrofit mobile x-ray cart to allow operator desired positioning of the DR console 250. As shown in FIG. 12, the mounting assembly 1200 can install without modifying an exterior, interior components and/or certification of the retrofit mobile x-ray cart.

As shown in FIG. 12, the mounting assembly can include a first connecting unit 1210, an engagement unit 1220 (e.g., rollers), a mounting arm 1230, and a mounting bracket 1240 for the DR console. In one exemplary embodiment, the first connecting unit 1210 can include a first cover plate 1212 to connect to existing engagement recesses in the tube tower 1105 and a second cover plate 1214. The first cover plate 1212 can include holes for threaded or nut/bolt connection to the existing recesses (e.g., original cover plate screw holes) in the tube tower 1105. The second cover plate 1214 can connect to the first cover plate 1212 and extend vertically down and outside the tower 1105 to provide a secure mount for one or more curved arms 1232 of the mounting arm 1230.

The engagement unit 1220 can be rigidly attached to or integral with the mounting bracket 1240 for the DR console 250. The engagement unit 1220 can provide a sliding connection between the mounting bracket 1240 and the mounting arm 1230. For example, the engagement unit 1220 can include rollers 1222 as shown in FIG. 12 or an annular ring, surrounding tube or the like to allow independent sliding of the bracket 1240 mounted DR console 230 along the mounting arm 1230 and a stopper 1224 to limit the independent rotational movement of the DR console 230 along the one or more arms 1232. In one embodiment, the arms 1232 can extend along a prescribed curve, ellipsoid, spline, etc. around the tube tower 1105. Further, the mounting arm 1230 can include a prescribed inner cross-section (e.g., circular, oval, rectangular, etc.) corresponding to the prescribed cross section (e.g., circular, oval, rectangular, etc.) of the engagement unit 1220. The mounting arm 1230 and engagement unit 1220 slidingly connect the DR console 230 to the retrofit mobile x-ray cart to rotate around the tube tower 1105.

As shown in FIG. 11C, the mounting assembly 1100 can extend a prescribed height 1160 above the tube tower 1105. For example, the prescribed height 1160 can be approximately 2 inches/5.08 cms. In contrast, the mounting assembly 1200 does not extend above the tube tower 1105 and can fit within a height profile of the original single mode mobile x-ray system. In one embodiment, the mounting assembly 1200 can be thinner than the original cover plate and can reduce a height profile of the retrofit DR dual mode mobile x-ray cart. Thus, in one embodiment, the retrofit DR dual mode mobile x-ray cart using the mounting assembly 1200 can fit within a three-dimensional footprint of the single mode mobile x-ray system.

As known to one or ordinary skill in the art, additional mechanical mechanisms can be used to rotatably couple the mounting arm to the tube tower, however, preferably for the mounting assembly (e.g., 1100, 1200), a height of the retrofit tube tower is not increased (or decreased) and the DR console can move (e.g., rotate) independently of and with the tube tower.

Figure 13A:
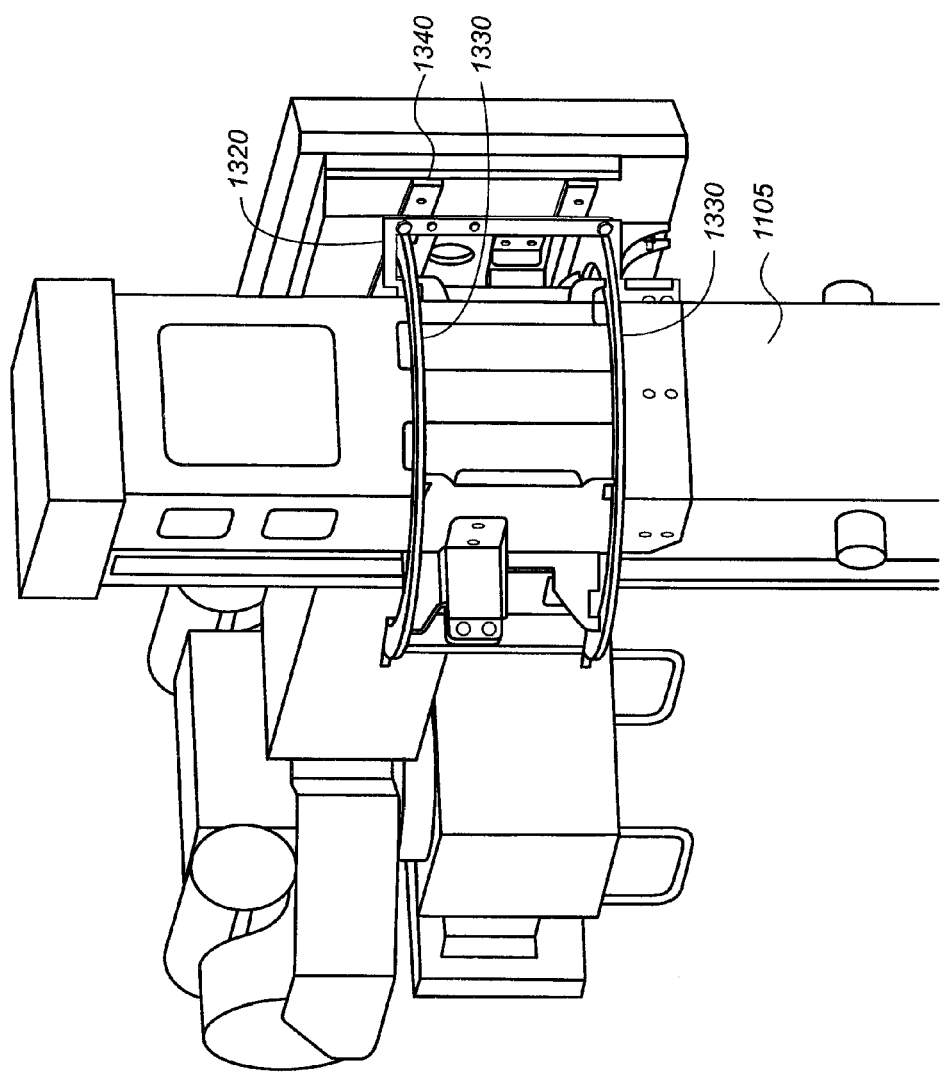
FIGS. 13A-13B are diagrams that show yet another exemplary mounting assembly for the DR display/controller in a retrofit apparatus according to embodiments of the application.
Figure 13B:
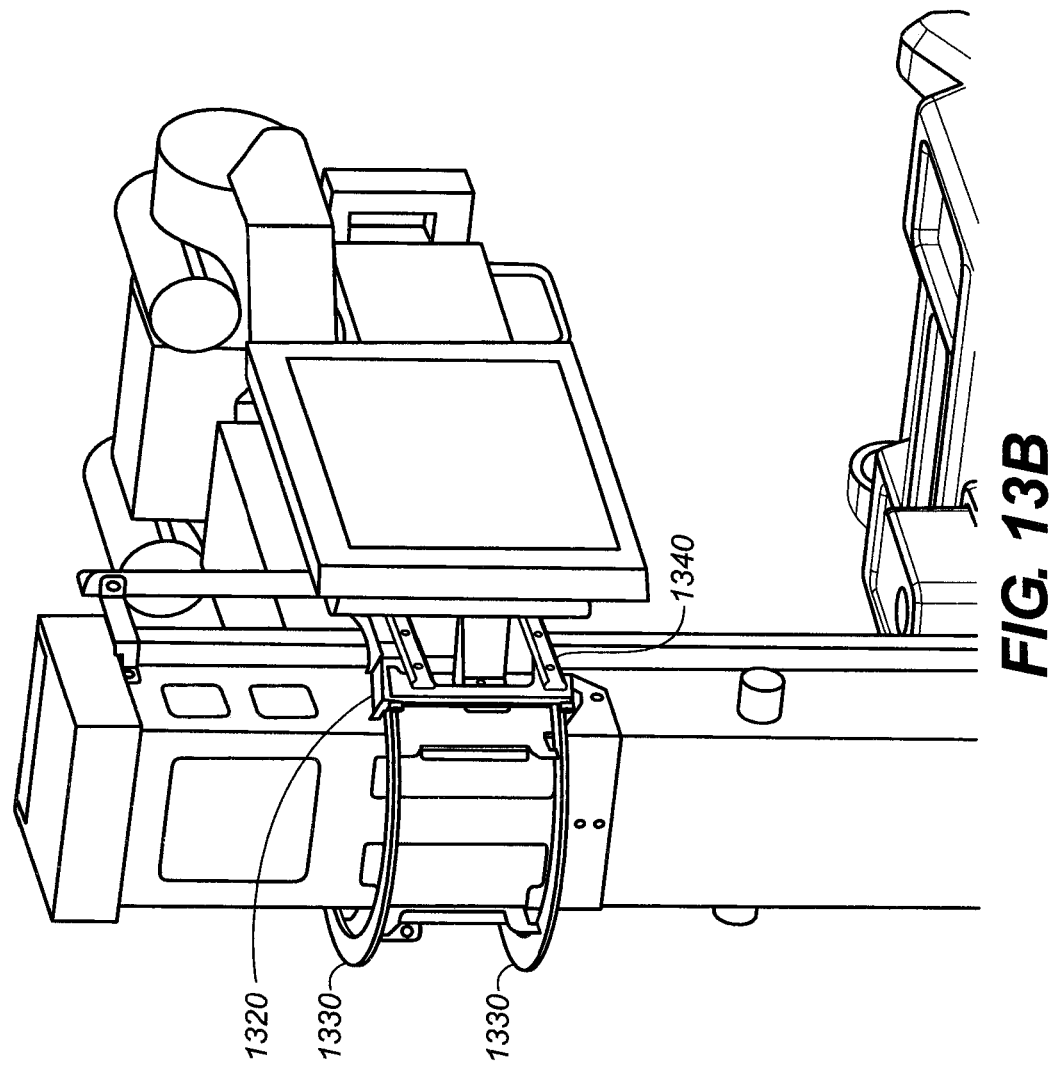

FIGS. 13A-13B are diagrams that show another exemplary embodiment of a mounting assembly of a DR console for a retrofit DR dual mode mobile x-ray cart. As shown in FIGS. 13A-13B, an engagement unit 1320 can provide a sliding connection between the mounting bracket 1340 and the mounting arm 1330. For example, the engagement unit 1320 can include surround the mounting arm 1330 to provide the sliding connection. Rollers (not shown) can be mounted inside the surrounding structure of the engagement unit 1320. The engagement unit 1320 can apply pressure to the mounting arm 1330 from at least two inside surfaces, three inside surfaces or all (e.g., four) inside surfaces to support or guide the mounting arm 1330.

Alternatively, the connector (e.g., 942) or the digital interface controller 940 can be configured to mechanically control exterior mounted preparation/exposure operator switches on the operator console of the film type mobile x-ray cart. For example, an operator interface can be formed by mounting a device (e.g., a second switch) that covers at least one exposed switch of the film type mobile x-ray imaging system. The second switch can operate to control a setting of at least the first switch (e.g., film type mobile x-ray cart preparation/exposure switch) according to a setting of second switch by an operator, which is dependent on a selected mode in the retrofit dual mode mobile x-ray cart.

In one embodiment, the DR mode can be operated/implemented by programmed control logic in the retrofit dual mode mobile x-ray cart. For example, the programmed control logic can include a processor and display, an integrated computer system, a portable computer or an integrated display.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method for obtaining an image by using a digital radiography receiver in a mobile x-ray imaging system of a first type configured for film radiography or computed radiography (CR), the method comprising:
    providing a mobile x-ray imaging system of a first type configured for film radiography or CR, the mobile x-ray imaging system comprising a first portable power source for the first type mobile x-ray imaging system;
    providing a mobile retrofit connection apparatus to operate the mobile x-ray imaging system in a first mode for use with a digital radiography receiver by:
    forming a receiver interface for communicating signals to and from the digital radiography receiver;
    forming an operator interface for routing at least a first operator imaging signal from an operator control to the retrofit connection apparatus;
    transmitting at least a second imaging signal from the mobile retrofit connection apparatus to an x-ray generator of the x-ray imaging system; and
    providing a second portable power source for the retrofit connection apparatus;
    in response to the first operator imaging signal routed over the operator interface channel, transmitting the second imaging signal to the x-ray generator; and
    providing the mobile retrofit connection apparatus a second mode to operate the mobile x-ray imaging system for use with a film receiver or a CR cassette,
    where the mobile retrofit connection apparatus does not change interior components of the mobile x-ray imaging system used in the second mode.

2. The method of claim 1 where the mobile retrofit connection apparatus does not require an electrical certification of the first type mobile x-ray imaging system or a physical configuration certification of the first type mobile x-ray imaging system.

3. The method of claim 1, where the mobile retrofit connection apparatus is connected to the first type mobile x-ray imaging system using existing fasteners, external fasteners, exposed fasteners, existing connectors, external connectors, or exposed connectors.

4. The method of claim 1, where the mobile retrofit connection apparatus does not change an exterior of the first type mobile x-ray imaging system, where the first portable power source or the second portable power source comprises an AC connector, a connector for connection to an external power source, a battery, or a rechargeable power source.

5. The method of claim 1 where forming a receiver interface further comprises providing a wireless communication link between the mobile retrofit connection apparatus and the digital radiography receiver or a physical communication link between the mobile retrofit connection apparatus and the digital radiography receiver.

6. The method of claim 1 where the operator control is a single manually operated actuator used in both the first mode and the second mode to generate the first operator imaging signal.

7. The method of claim 6, where the mobile x-ray imaging system uses the same single manual actuator as an operator interface in the first mode and the second mode, where the single manual actuator is a press button, a rocker switch, a toggle switch, two switches, a handheld switch, a touch screen or a tethered actuator.

8. The method of claim 1, further comprising providing the mobile retrofit connection apparatus with a variable preset delay timer set according to operations of an x-ray source of the x-ray imaging system, where the variable preset delay timer is set according to x-ray tube rotor spin up or anode current generation at the x-ray imaging system.

9. The method of claim 1 further comprising providing a mode selector that selects an alternate timing sequence in the first mode and the second mode, where the second imaging signal is directly provided as an output expose signal upon receipt of the first operator imaging signal in the second mode.

10. The method of claim 1 further comprising sensing an x-ray anode current level at least during image exposure, and terminating signal integration on the digital radiography receiver according to the sensed x-ray anode current level.

11. The method of claim 1 where forming an operator interface comprises disconnecting at least one control switch from a first connector comprised in the mobile x-ray imaging system and connecting the at least one control switch to a second connector comprised in the retrofit connection apparatus, and where the x-ray film receiver or the CR cassette are removed from the mobile x-ray imaging system to output an image and the digital radiography receiver is not removed from the mobile x-ray imaging system to output an image.

12. The method of claim 1 where forming an operator interface comprises mounting a device that covers at least one exposed switch of a film type mobile x-ray imaging system.

13. The method of claim 1 where providing a mobile retrofit connection apparatus comprises providing a DR console for use in the first mode setting, where providing the DR console comprises,
    replacing a cover plate at a top of a tower of the mobile x-ray imaging system;
    affixing a mounting bracket to a side of the DR console; and
    rotatably installing a mounting arm between the mounting bracket and a replacement cover plate, where the DR console can rotate concurrently with the tower and the DR console can rotate independently around at least 180 degrees of the tower, and where the providing the DR console does not increase a height of the tower.

14. An apparatus configured to obtain an image using a second digital mode in a single mode mobile x-ray imaging system, comprising:
    an x-ray generator of a single mode mobile x-ray imaging system;
    a generator interface to communicate with the x-ray generator of the single mode mobile x-ray imaging system;
    a first portable power source for the single mode mobile x-ray imaging system; and
    an interface component installed as a retrofit to the single mode mobile x-ray imaging system, the interface component comprising:

a mode selector to select at least a first mode setting for image capture using a digital radiography receiver and a second mode setting for image capture using the single mode;

a receiver interface to communicate with the digital radiography receiver;

an operator interface to communicate with an operator control for receiving at least one imaging signal; and a programmed control logic processor that, when the first mode setting is selected, responds to the at least one imaging signal to control an exposure captured by the digital radiography receiver.

15. The apparatus of claim 14 where the interface component does not change interior components of the single mode mobile x-ray imaging system, where the interface component further comprises a second portable power source for the interface component.

16. The apparatus of claim 14 where the x-ray generator is mounted on a fixed structure, mounted on an adjustable structure, mounted on a telescoping structure, mounted on a telescoping adjustable structure, mounted on a structure adjustable in two dimensions or mounted on a structure adjustable in three dimensions, where the receiver interface comprises a wireless or physical communication link for use between the interface component and the digital radiography receiver, and where the mode selector provides an instruction to the programmed control logic processor.

17. The apparatus of claim 14 where the interface component further comprises at least a sensor for x-ray anode current level of the x-ray generator or a sensor for providing a signal indicative of x-ray emission according to a sensed electrical current level, where the single mode is configured to use a removable film or removable computed radiography cassette.

18. The apparatus of claim 14 where the operator control is a single manually operated actuator used in both the first mode setting and the second mode setting to generate the at least one imaging signal, and where the at least one imaging signal comprises a first, preparation signal or a second, expose signal from the operator.

19. The apparatus of claim 14 where the generator interface further comprises a switch controller for covering at least a first switch on a control panel of the single mode mobile x-ray imaging system and for controlling the setting of at least the first switch according to a setting of a second switch by an operator.

20. The apparatus of claim 14 where the interface component further comprises a DR console mounting assembly, where the DR console mounting assembly comprises, a first connection unit to replace a cover plate of a tower of the mobile x-ray imaging system;

a second connection unit to attach to the DR console; and a mounting arm rotatably installed between the second connection unit and the first connection unit, where the DR console can rotate concurrently with the tower and the DR console can rotate independently around at least 180 degrees of the tower, and where the DR console mounting assembly does not increase a height of the tower.

* * * * *